United States Patent [19]

Miwa et al.

[11] Patent Number: 4,878,914
[45] Date of Patent: Nov. 7, 1989

[54] CERAMIC PROSTHESIS FOR LIVING BODY & METHOD OF MAKING THE SAME

[75] Inventors: Takeru Miwa; Iwao Noda, both of Shiga, Japan

[73] Assignee: Kyocera Corporation, Kyoto, Japan

[21] Appl. No.: 214,874

[22] Filed: Jul. 1, 1988

Related U.S. Application Data

[63] Continuation of Ser. No. 758,101, Jul. 23, 1985, abandoned.

[30] Foreign Application Priority Data

Jul. 23, 1984 [JP] Japan .................................. 59-153582

[51] Int. Cl.$^4$ ............................ A61F 2/28; A61F 2/30
[52] U.S. Cl. ......................................... 623/16; 623/18; 623/66; 428/325; 427/2; 427/376.2
[58] Field of Search ...................... 501/1, 80, 153, 154; 623/16, 66, 17-23; 428/325, 426, 688; 427/2, 376.2

[56] References Cited

U.S. PATENT DOCUMENTS

| | | | |
|---|---|---|---|
| 4,073,999 | 2/1978 | Bryan et al. | 623/16 X |
| 4,082,863 | 4/1978 | Dancy et al. | 427/202 X |
| 4,103,002 | 7/1978 | Hench et al. | |
| 4,168,326 | 9/1979 | Broemer et al. | 427/2 |
| 4,177,524 | 12/1979 | Grell et al. | 427/2 X |
| 4,221,748 | 9/1980 | Pasco et al. | 623/16 X |
| 4,223,412 | 9/1980 | Aoyagi et al. | 623/16 |
| 4,237,559 | 12/1980 | Borom . | |
| 4,309,488 | 1/1982 | Heide et al. | 623/16 X |
| 4,542,539 | 7/1985 | Rowe, Jr. et al. | 623/16 X |
| 4,547,327 | 10/1985 | Bruins et al. | 623/16 X |
| 4,550,448 | 11/1985 | Kenna | 623/16 |
| 4,644,942 | 2/1987 | Sump | 623/16 |
| 4,693,986 | 9/1987 | Vit et al. | 623/16 X |

FOREIGN PATENT DOCUMENTS 2134316 1/1972 Fed. Rep. of Germany .

*Primary Examiner*—Alan W. Camon
*Attorney, Agent, or Firm*—Spensley Horn Jubas & Lubitz

[57] ABSTRACT

A ceramic prosthesis for the living body wherein a plurality of globular or indefinite-shaped ceramic particles are bonded by sintering into one body directly or indirectly with the surface of a ceramic substrate of alumina ceramics, ziroconia ceramics or the like to permit the ingrowth of bone cells into gaps between the particles of the ceramic particles. The material is very suitable for a prosthesis such as an artifical joint in that the material is enabled to provide stront bonding and fixing thereof to the living bone by permitting early ingrowth of bone cells in the living body and to provide stability of the bonding and fixing over a long period of time.

13 Claims, 1 Drawing Sheet

CERAMIC PROSTHESIS FOR LIVING BODY & METHOD OF MAKING THE SAME

This is a continuation of application Ser. No. 758,101 filed on 7/23/85, now abandoned.

BACKGROUND OF THE INVENTION:

1. FIeld of the Invention

This invention relates to a prosthesis for the living body used for restoring the missing function and hard tissue in the living body brought about by diseases and accidents and to a method of making the same.

2. Prior Art

When people are deprived of the articular function of their limbs by a disease such as rheumatoid arthritis which predilectly attacks women of 20 to 40 years of age, an operation for replacing the lost function of the joint by an artificial bone is often performed as one of surgical therapeutic methods in addition to pharmaceutical therapy, and is conducted mostly in the treatment of hip joints and knee joints.

Presently, artificial joints are mostly made of metal and plastic as a raw material and are extensively used in an artificial hip joint, knee joint, shoulder joint, finger joint and the like. The greatest problem common to those artificial joints lies in loosening (i.e. getting loosened during use). Namely, several years after an artificial joint replacement operation, there occurs a loosening between the joint and the bone and the loosening causes pain and reduction in the function of artificial joint with the result that there are not a few instances wherein removal of the artificial joint and reoperation must be performed.

In an artificial joint replacement operation, an acrylic resin referred to as bone cement is used during the operation in order to bond the artificial joint to the epiphysis of bone but the use of the bone cement involves following disadvantages (1) that because the resin generates a heat of 70° to 80° C. when it is polymerized and solidified, such heat of polymerization solidifies protein of the bone and soft tissue to bring them into necrosis, (2) that the monomer left during polymerization also has toxicity, From the disadvantages in (1) and (2), it may result that although the use of the bone cement provides firm bonding between the necessary portions of the bone in a shortened period of operation, the cement constitutes one factor in the loosening of the bone portion in a later day. Furthermore, in the case of a metallic artificial joint, it is hard to prevent corrosion of the metal material in the human body and there is a danger of metallic ions producing harmful effects on the body to bring the living body into necrosis.

From this point of view, an alumina ceramic artificial joint has been developed which is free from corrosion in the body and can be conglutinated into one body with the bone without the use of bone cement because of its excellent biocompatibility with the bone, and has widely been used in many joints of the human body such as knee joint, foot joint. However, the alumina ceramics is excellent in stability and high in mechanical strength in the living body, while because it is an inert material, it takes a considerably long period of time before it comes to conglutinate with a natural bone and is solidified after implantation, if the ceramic surface is smooth. Accordingly, in order to promote conglutination of the artificial joint with the bone, the art of forming large and small grooves on the surface of the alumina artificial joint was proposed. The grooves are effective for the prevention of lateral slip of the artificial joint and for fixing the artificial joint in proper position to the bone, but are liable to be short in anchoring effect (catching effect) in the direction of vertical tension with respect to the bone surface, and then it takes a long time to fix the artificial joint to the bone with the aid of the grooves in contrast to bonding time by use of bone cement. This is a problem concerning an artificial joint of alumina ceramics.

SUMMARY OF THE INVENTION

This invention is directed to removal of the drawbacks of the conventional implantable prosthesis of the described type and more particularly to the provision of an implantable ceramic prosthesis, especially a ceramic prosthesis which is devised to give a new surface shape to an artificial joint of ceramics.

The invention will now be described in greater detail with reference to embodiments thereof shown in the drawing.

DETAILED DESCRIPTION OF THE INVENTION

Referring now to making a test piece of the prosthesis of the invention, a ceramic slurry (later described) is applied to the surface of an green alumina substrate containing 99% by weight of alumina ($Al_3O_3$) (the term "by weight" is applicable hereinafter), the ceramic slurry (slurry prepared by adding an organic binder to powder of ceramic stock such as alumina, zirconia under kneading) consisting essentially of alumina and containing less than 10% of each of magnesia (MgO), silica ($SiO_2$) and yttria ($Y_2O_3$) as a sintering agent and having an organic binder mixed therewith. On the substrate thus applied with the ceramic slurry are dispersedly placed green alumina particles (99% of alumina) of mean particle size of 125 to $3100\mu$ (corresponding to 100 to $2500\mu$ after sintering) in the range of distribution density of 9–3200 particles/$cm^2$ (corresponding to a distribution density of 16 to 50,000 particles/$cm^2$ after sintering) to a thickness of a single to several layers. The substrate thus treated is dried well and sintered at 1300° to 1800° C. to obtain a test piece. Further, for the purpose of increasing the bonding strength of ceramic particles to the substrate it may be possible to add less than 30% of silica type glass component to the ceramic slurry or to coat alumina particles with the ceramic slurry. In the above, a description has been given of the case wherein both the substrate and the particles are green, it should be understood that one or both of the substrate and ceramic particles may be of sintered body or of temporarily fired (biscuit-fired) body. The ceramic particles are preferably of globular shape as are used in the later Examples, but shape may be applied as the case may be.

EXAMPLE 1

To both surfaces of an green substrate containing 99% of alumina was applied to a thickness of 0.1 to 0.3 mm a slurry consisting essentially of alumina and containing less than 10% of each of magnesia, silica and yttria and having an organic binder mixed therewith. Green alumina particles of 300 to 450μ in mean particle size which were coated with the slurry to a thickness of 20 to 40μ were sprinkled on both sides of the thus treated substrate in three layers to a distribution density of 1000 to 2000 particles/cm². The substrate thus treated was left overnight to dry at room temperature and was thereafter sintered at 1700° C. to make the alumina particles sintered over the substrate to fabricate a test piece. The test piece obtained was reduced to 80% of the original size in length, width and thickness by sintering contraction and the test piece size after sintering was 10 mm×10 mm×about 4 mm. The particle size of the particles was 250 to 350μ.

Figure 2:
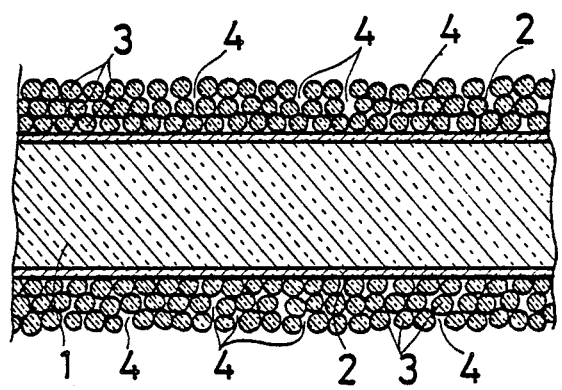
FIG. 2 is a view similar to FIG. 1 but showing another embodiment of the implantable prosthesis of the invention.
Figure 3:
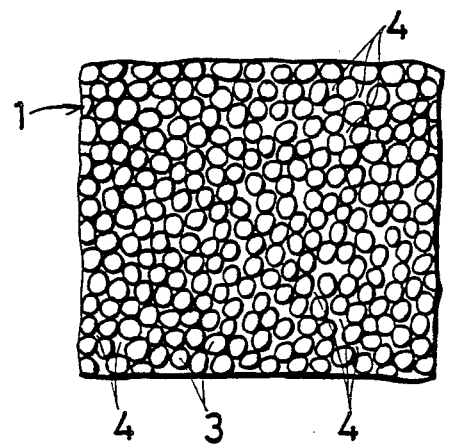
FIG. 3 is a plan view of FIG. 2.

Referring to the thus fabricated test piece shown in FIG. 2, the numeral 1 designates an alumina ceramic substrate; 2 designates a thin ceramic layer formed over the substrate by ceramic slurry coating and sintering; and 3 designates alumina ceramic particles sprinkled on and bonded to the layer 2 in three layers with gaps 4 each of 100 to 150μ formed between the particles.

Each of the test pieces produced in the manner described above was sterilized in an autoclave and was implanted into the condyle of tibia of a rabbit. After a lapse of four, eight, twelve and twenty-four weeks subsequent to the implantation, the rabbit was killed after tetracycline labelling and the bone containing the test piece was taken out of the rabbit. After the bone was subjected to formalin fixing and was made into an undecalcified test piece and a state of bonding of the test piece to the natural bone was observed by the use of an optical microscope etc.

Microscopic examination showed that although the substrate which passed four weeks after implantation was covered with a new bone, the bone merely surrounded the whole of the test piece. But in the case of the test piece which passed 8 weeks after implantation, the ingrowth of the bone was noticed between the gaps formed by the alumina ceramic particles and it was observed that this tendency was becoming stronger in proportion to a lapse of time, say, from 12 weeks to 24 weeks in such a manner that in the test piece which passed 24 weeks, bone cells grew far into the depths of the gaps between three layers of ceramic particles with a new bone grown into bond with the surface of alumina ceramics.

It was ascertained from the above experiment that, although the alumina substrate used was of inert alumina on the surface, the growth of bone tissue into the gaps formed between the alumina particles proved effective and alumina ceramics was bonded directly to the natural bone.

EXAMPLE 2

Alumina ceramic particles each having a mean particle size of 250 to 350μ were sprinkled on and bonded to the alumina substrate in the range of 2000 to 3000 particles/cm² in the same manner as in Example 1 to fabricate a test piece of the same size to be classified into group A, while test pieces each of alumina ceramic particles having a mean particle size of 1000 to 1500μ and bonded to the substrate in the range of 200 to 300 particles/cm² were classified into group B. The alumina substrate used as a reference test piece and having no alumina ceramic particles bonded thereto was used as a contrat test piece and classified into group C.

Each of the test pieces obtained in the above manner was sterilized in an autoclave and was implanted into the condyle of tibia of a rabbit. The natural bones including the test pieces were taken out of the rabbits killed after a lapse of 8, 12, 24 and 36 weeks, respectively. The test pieces were shaved off by a dental bar in the neighborhood of the pieces, respectively, to form analytes each having a shape adapted to have it hooked. Thereafter, each of the test pieces and the bones was hooked and subjected to tension test by Instron (an U.S. maker's name) type universal tester at a crosshead speed of 5 mm/min to test the bonding strength of the test pieces bonded to natural bones. The result of the tension test is shown in the following table.

| Data | Group A | Group B | Group C |
|---|---|---|---|
| Mean particle size | 250–350μ | 1000–1500μ | not fixed |
| Tension strength after | | | |
| 8 weeks | 6.4 kg | 2.6 kg | 0.5 kg |
| 12 weeks | 8.8 kg | 6.1 kg | 1.1 kg |
| 24 weeks | 10.1 kg | 10.8 kg | 1.5 kg |
| 36 weeks | 10.3 kg | 19.5 kg | 1.6 kg |

The result obtained after 8 weeks shows that the alumina ceramic substrate (group A) having alumina ceramic particles of 250 to 350μ in mean particle size bonded thereto was bonded to the natural bone with bonding strength about 13 times as high as that of the simple substance substrate of alumina ceramic (group C), but the alumina ceramic substrate having ceramic particles of 1000 to 1500μ attached thereto (group B) was about five times as high in bonding strength as group C. The reason is presumed to be that the gaps between the alumina ceramic particles of 250 to 350μ in mean particle size provide gaps of 100 to 150μ suitable for growth of bone tissue thereinto. This can be endorsed by the fact that the gaps between the alumina ceramic particles of 1000 to 1500μ in group B are as wide as 400 to 600μ and delay in the ingrowth of bone cells is attributable to the provision of bonding strength less than half as much as the strength of group A. As shown by the experiment, in the case of the alumina ceramic substrate having alumina ceramic particles of 250 to 250μ in mean particle size bonded thereto, the anchor effect produced by growth of bone cells into the gaps between the particle provided a great bonding strength in a short time after the operation. But as shown in Example 1, the result obtained 24 weeks after the operation during which the bone cells have grown deep into three layers of alumina ceramic particles shows that the test pieces of group A were only about one and half times as high in bonding force as those which passed 8 weeks after the operation and even those which passed 36 weeks showed no substantial improvement. It was microscopically confirmed from the analytes that the reason for this is that in the small gaps between the alumina ceramic particles each having a particle size (250 to 350μ) such as those in group A, the bone cells are enabled to make bone ingrowth from an early stage of implantation but these cells are immatured bone cells including a plurality of osteoblasts and, because the gaps are small, are not allowed to grow fully.

On the other hand, in group B, bonding strength is increased with a lapse of time and 24 weeks after the operation it exceeds the measured value of group A, proving to be about one and half times as high as that of the analyte obtained 8 weeks after the operation. In the analyte obtained 36 weeks after the operation the bonding strength was about twice as high as that obtained 24 weeks after the operation. This value was about 12 times as high as that of the contrast example of group C and about 1.9 times higher than the analyte of group A. The reason why longtime implantation has provided such a high value was confirmed by microscopic observation. Namely, in the test piece of group B 12 weeks after the operation, not only the bone cells grew deep into the gaps between the alumina ceramic particles but also progress was made in the remodelling of bone to allow bone cells to grow sufficiently to form close and well-built bone in layers. And there was noticed substantially no osteoclast such as giant cell and integration of the particles with the bone was in an ideal state such that the bone cells were firmly intertwined with the complicated gaps formed by three layers of particles. The high value of bonding force of the analytes in group B resulted from sufficient bonding of interface between the bone and the ceramic substrate. Accordingly, it was confirmed that the alumina substrate in group B having alumina ceramic particles of 1000 to 1500$\mu$ in mean particle size bonded thereto has a little to be conducive to bonding to the natural bone at an early stage of implantation but contributes to stable and sufficient bonding in long-term implantation.

The alumina ceramic substrate shown in the examples and having alumina ceramic particles bonded thereto can produce the following effects when the substrate is applied to a ceramic artificial joint having no bone cement used therein. Namely, when alumina ceramic ceramic particles of 250 to 350$\mu$ are bonded to the alumina substrate, such bonding of the particles can impart to the substrate the initial fixing property of the artificial joint within a short time after the operation, which initial fixing property forms one of the objects of the invention, while on the other hand, when alumina ceramic particles of 1000 to 1500$\mu$ are bonded to the alumina ceramic substrate, such bonding is highly effective for measures against the loosening which is the greatest problem to the artificial joint in the living body when the joint is used over a long period of time.

What is developed and readily presumable from the examples above is that when experiments were made with the substrate having alumina ceramic particles bonded thereto in the range of two kinds of particles, sufficient bonding strength was imparted to the substrate over a short to long period of time, and experimentally, the substrate having 10 parts of alumina ceramic particles of 250 to 350$\mu$ in mean particle size mixed with one part of alumina ceramic particles of 1000 to 1500$\mu$ in mean particle size produced the best result, showing 5.5 kg in 8 weeks, 10.3 kg in 24 weeks, and 17.5 kg in 36 weeks, respectively after the operation.

Incidentally, it is known that the suitable gaps for bone cells to grow thereinto may be in the range of 100 to 300$\mu$ (optimumly) 100 to 150$\mu$), and in the invention, the gaps could be experimentally formed by alumina particles having 100 to 600$\mu$ in means particle size, and alumina ceramic particles having less than 100$\mu$ could merely form a small gap of less than 100$\mu$. On the other hand, the bonding strength of the alumina ceramic substance which passed the longest time after the operation (36 weeks) and which has alumina ceramic particles larger than 600$\mu$ bonded thereto exceeded 15 kg, and the optimum range of particle size is 1000 to 1500$\mu$. But alumina ceramic particle size exceeding 2500$\mu$ could be bonded to the alumina ceramic substrate, but could not be utilized from viewpoint of the design of an artificial joint, necessary strength and dimensional limit of the substrate itself.

With respect to the distribution density of the alumina ceramic particles to be bonded, it is desirable that the density be close enough to permit the formation of gaps in the range of 100 to 300$\mu$ adapted for bone ingrowth conducive to initial fixing property and, according to an experiment with alumina ceramic particles of 100 to 600$\mu$ in mean particle size, the optimum distribution density of forming such gaps was 1400 to 1600 particles per $cm^2$.

On the other hand, with respect to the thickness of an alumina slurry layer in making particles bonded to the alumina ceramic substrate, a relatively thin layer can provide sufficient bonding force because the substrate, alumina ceramic particles, slurry are of the material identical with each other and a thickness of 50 to 150$\mu$ is sufficient for the thickness of slurry layer relative to the alumina ceramic particles of 100 to 600$\mu$ in mean particle size. Even in the case of the alumina ceramic particles of 600 to 2500$\mu$ in mean particle size, a thickness of slurry layer of about 200 to 400$\mu$ produced good results. The thickness in which the alumina ceramic particles are coated with ceramic slurry is experimentally confirmed by the fact that, in the case of particles of 100 to 600$\mu$ in means particle size, a thickness of 20 to 100$\mu$ an in the case of the particle of 600 to 2500$\mu$ in mean particle size, a thickness of about 100 to 200$\mu$ provides sufficient bonding strength without preventing the formation of the gaps between alumina ceramic particles.

Furthermore, for the purpose of improving the bonding strength of the alumina ceramic particles to the substrate, there may be the case wherein glass consisting essentially of $SiO_2$ and/or $B_2O_3$ is mixed into the ceramic slurry. This case is applicable when strong bonding force is necessary as when the whole of an artificial bone or joint is placed under continuous dynamic load. To prevent the alumina ceramic particles from falling off the substrate, addition of the glass component within the range of less than 30% can improve the bonding strength. Addition of the glassy material in quantities in exess of 30% causes poor sintering of the whole of the slurry and greatly reduces bonding force.

In the above, mention has been made of the case wherein alumina ceramic particles are fixed to the alumina ceramic substrate surface, and it should be understood that, when a biomaterial is produced, use may be made of a zirconia ceramic substrate and zirconia ceramic particles which have biocompatibility and high mechanical strength.

Figure 1:
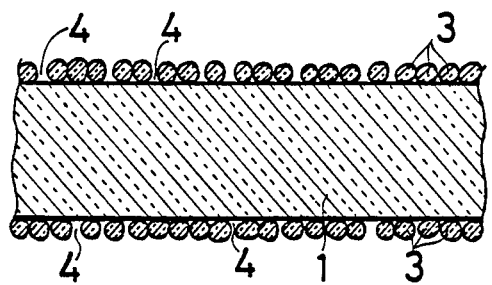
FIG. 1 is a longitudinal sectional view showing typically one embodiment of the implantable prosthesis of the invention.

As a structural modification of the invention, it is possible to sinter and bond the ceramic particles directly to the ceramic substrate without interposing a ceramic layer therebetween. FIG. 1 shows an example of the modification wherein like members are designated by like reference characters. The case wherein no ceramic layer is used as in the modification, namely, no ceramic slurry is used is limited to the fact that both or either of the ceramic substrate and the ceramic particles are green body or temporarily fired body and both can be sintered into one body through heating. When both the substrate and the particles start from sintered body, the formation of the ceramic layer is essential for bonding both of them.

As described above, the essential point of the invention lies in the bonding of ceramic particles such as of alumina ceramics, zirconia ceramics to the ceramic substrate, and accordingly the production of a prosthesis is easy and moreover, because the bonding is effected not by secondary glass bonding but by sintered bonding between the ceramic substrate and the slurry of the same material as the substrate, the bonding force of the ceramic particles is great and offers little possibility of the particles falling off the substrate during use. Moreover, by coating also the surface of the ceramic particles with the slurry it is also possible to bond the particles to the substrate in multiple layers.

The invention makes it possible to facilitate ingrowth of bone cells and provide early and strong bonding and fixing by suitably selecting the particle size and distribution density of ceramic particles to be fixed, namely by using particles of 250 to 350μ in mean particle size, depending upon the place and object of use. The invention further renders it possible to obtain stronger bonding and fixing and long-term stability in a later stage of implantation by the bone cells coming into full growth by the use of ceramic particles of 1000 to 1500μ in mean particle size. Thus, the invention provides superior prostheses and members for the living body such as an artificial joint, artificial bone which are effective for the prevention of the loosening which constitutes the greatest problem in artificial joints.

We claim:

1. A prosthesis, comprising:
    a ceramic substrate;
    a ceramic layer formed of ceramic particles said layer comprising a mixture of a first group of ceramic particles and a second group of ceramic particles, the first group of ceramic particles having a mean diameter within the range of 250 to 350μ, the second group of ceramic particles having a mean diameter within the range 1,000 to 1,500μ, the ceramic layer also having interconnected gaps formed between substantially all of the ceramic particles, the gaps having a mean size less than the mean diameter of the particles; and
    a layer of sintered ceramic bonding the layer of ceramic particles to the ceramic substrate, the interconnected gaps of the ceramic layer forming a network into which bone tissue may grow.

2. A prosthesis according to claim 1, wherein the ceramic substrate, the layer of ceramic particles, and the layer of sintered ceramic are formed of the same type of ceramic material.

3. The prosthesis according to claim 2, wherein the same type of ceramic material comprises alumina ceramic.

4. A prosthesis according to claim 2, wherein the same type of ceramic material comprises zirconia ceramic.

5. A prosthesis according to claim 1, further comprising:
    a second ceramic layer formed of ceramic particles, the second ceramic layer having gaps formed between substantially all of the particles, wherein the particles and gaps of the second ceramic layer are of approximately the same means size as the particles and gaps of the ceramic layer; and
    a second layer of sintered ceramic bonding the second ceramic layer to the exposed surface of the ceramic layer opposite the ceramic substrate.

6. A prosthesis according to claim 1, wherein the layer of sintered ceramic contains at least one component of glass selected from the group consisting of $SiO_2$ and $B_2O_3$.

7. A prosthesis according to claim 1, wherein the first group of ceramic particles of the ceramic layer forms gaps between the particles having a mean size of 100 to 150μ.

8. A prosthesis according to claim 1, wherein the ceramic particles of the ceramic layer have a mean diameter size of 1000 to 1500μ and the gaps formed between the particles have a means size of 400 to 600μ.

9. A prosthesis according to claim 1, wherein said ceramic particles are bonded to the surface of said ceramic substrate in a density of distribution of 16 to 50,000particles/cm².

10. A prosthesis according to claim 9, wherein the density of distribution of said first group of particles is between 2000 and 3000 particles/cm².

11. A prosthesis according to claim 9, wherein the density of distribution of said second group of particles is between 200 and 300 particles/cm².

12. A prosthesis according to claim 6, wherein said glass comprises up to 30% of said layer of sintered ceramic.

13. A prosthesis, comprising:
    a ceramic substrate; and
    a ceramic layer formed of ceramic particles, said layer comprising a mixture of a first group of ceramic particles and a second group of ceramic particles, the first group of ceramic particles having a mean diameter within the range of 250 to 350μ, the second group of ceramic particles having a mean diameter within the range of 1000 to 1500μ, the ceramic layer having interconnected gaps formed between substantially all the ceramic particles, the gaps having a mean size less than the mean diameter of the particles, wherein the ceramic particles are sintered and bonded directly to said ceramic substrate.

* * * * *